United States Patent

Parkinson

[11] Patent Number: 6,019,734
[45] Date of Patent: Feb. 1, 2000

[54] DIAGNOSTIC TEST FOR VAGINAL INFECTIONS

[76] Inventor: Chris Parkinson, 166 Emerald Street South, Suite 2, Hamilton, Canada, L8N 2V7

[21] Appl. No.: 08/985,233

[22] Filed: Dec. 4, 1997

[30] Foreign Application Priority Data

Dec. 4, 1996 [CA] Canada .................................. 2192004

[51] Int. Cl.[7] .................................................. A61B 5/00
[52] U.S. Cl. ........................................ 600/572; 600/584
[58] Field of Search .................................. 600/562, 572, 600/573, 584

[56] References Cited

U.S. PATENT DOCUMENTS

| | | | |
|---|---|---|---|
| 4,862,899 | 9/1989 | Bucaro | 600/572 |
| 5,140,986 | 8/1992 | Klinger | 600/572 |
| 5,353,803 | 10/1994 | Cerra | 600/562 |
| 5,425,377 | 6/1995 | Caillouette | 128/759 |
| 5,735,801 | 4/1998 | Caillouette | 600/572 |

*Primary Examiner*—Max Hindenburg
*Attorney, Agent, or Firm*—Burns, Doane, Swecker & Mathis, L.L.P.

[57] ABSTRACT

An apparatus, method and diagnostic kit for assessing the presence or absence of a vaginal infection including bacterial vaginosis which includes a pH indicator means and a KOH patch for detecting bacterially derived amines. A method, apparatus and test kit for diagnosing vaginosis in a simple test series which can be readily performed in a doctor's office at the time a vaginal fluid sample is taken.

21 Claims, 1 Drawing Sheet

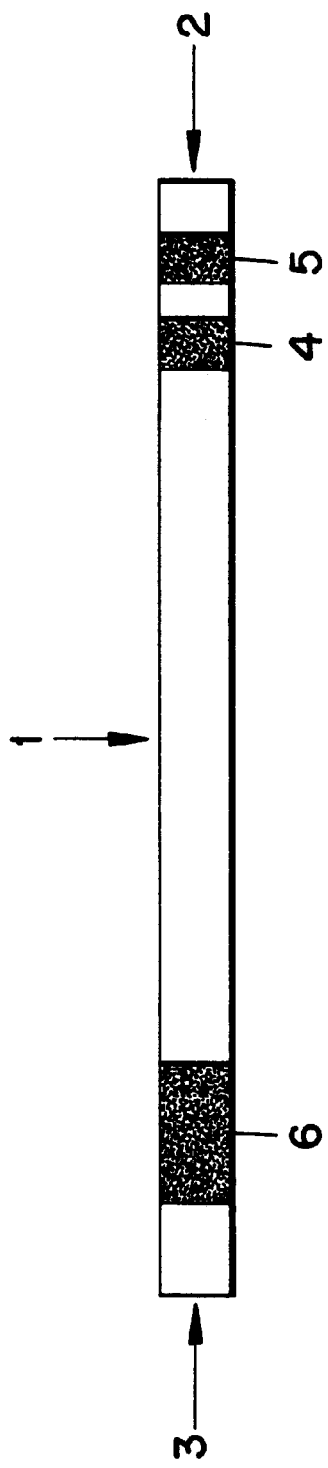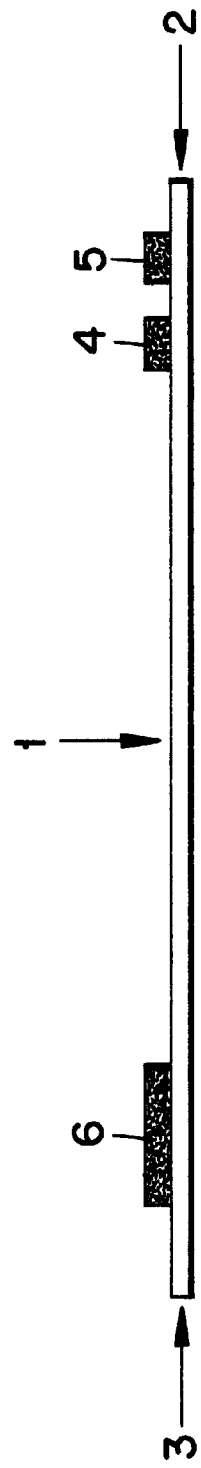

DIAGNOSTIC TEST FOR VAGINAL INFECTIONS

FIELD OF THE INVENTION

The present invention relates generally to a diagnostic test for vaginal infections including bacterial vaginosis. It includes a rapid, easy, self-contained, noninvasive method of diagnosing bacterial vaginosis which conforms to accepted diagnostic guidelines and can be performed in a physician's office.

BACKGROUND OF THE INVENTION

Bacterial vaginosis ("BV") is a common, underdiagnosed condition afflicting millions of women in North America alone. Left untreated, BV can cause pelvic inflammatory disease, premature rupture of membrane, pre-term labour, and post-abortal and post-hysterectomy infections. Currently, diagnosis of BV occurs in two ways.

Firstly, the physician may diagnose BV by ordering a complete microbiological workup which involves the physician obtaining a sample of vaginal fluid, labeling the sample, packaging the sample and sending the specimen to a laboratory for analysis. This results in a two to four day turn around to receive the results from the laboratory. In addition, laboratory analysis of a vaginal smear is expensive.

Secondly, a diagnosis of BV may be made by the physician in his or her office when three or four criteria are met: 1) presence of clue cells; 2) an indicative vaginal discharge; 3) a pH of vaginal fluid greater than or equal to 4.5; and 4) a positive potassium hydroxide ("KOH") "whiff" test. (The four criteria are often referred to as the Amsel Criteria.)

The first criteria (criteria 1) is the presence of clue cells. To test for the presence of clue cells in the physician's office, the physician does a wet mount or gram stain where a swab of the vaginal fluid is taken and applied to a slide which the physician examines under the microscope. However, many physician do not routinely utilize microscopes in their office. If the physician does not wish to use a microscope, the physician must label, package and send the specimen to a laboratory, resulting in the above-referred to two or four day turn around in order to receive the results from the laboratory.

The second criteria (criteria 2) is the presence of an indicative vaginal discharge which is thin and homogeneous grey to white.

The third criteria (criteria 3) is a pH of the vaginal fluid which is equal to or greater than 4.5. Traditionally, the physician has had to manipulate pH paper to perform this test. This awkward and cumbersome.

The fourth criteria (criteria 4) is a positive KOH "whiff-test". Traditionally, the physician has performed this test by applying one to two drops of 10%–20% KOH solution to vaginal fluid which has been smeared on a slide. The physician then smells the sample. If the sample gives off a foul odour of dead fish, it is indicative of the presence of bacterially-derived amines including putrescine, cadverine, spermine and spermidine, which is therefore indicative of BV. The KOH whiff test has been, to date, cumbersome for the physician to perform.

Involving a laboratory in diagnosis can lead to delays in diagnosis of BV or the use of non-specific therapies being prescribed in the interim. To date, if the physician performs the diagnosis in his or her office, the need to manipulate various different apparatus as well as caustic substances such as KOH can possibly lead to delays in diagnosis or non-diagnosis of BV, also leading to non-specific therapies being prescribed or no therapy at all. Furthermore, there is a movement in the medical field, including by various societies of Obstetricians and Gynecologists, towards regular and routine screening of certain women for BV.

There is a need for a simple, self-contained, rapid and specific diagnostic test for BV that conforms to accepted diagnostic guidelines, can be performed in the physician's office and overcomes the problems mentioned above. If BV is ruled out, there is a need to determine the pH of vaginal fluid to assist in the diagnosis of other vaginal infections such as yeast infections.

SUMMARY OF INVENTION

In accordance with an aspect of the present invention, there is provided an apparatus for testing vaginal fluid for accessing the presence or absence of a vaginal infection, the apparatus comprising:

one or more carrier means, a patch impregnated with an effective amount of potassium hydroxide applied to one of the carrier means, and a first pH indicator means applied to one of the carrier means, whereby the apparatus is adapted to receive one or more vaginal fluid samples on each of the potassium hydroxide patch and the first pH indicator means.

In accordance with a further aspect of the invention, there is provided an apparatus for testing vaginal fluid for assessing the presence or absence of a vaginal infection, the apparatus comprising:

a carrier means, and a patch impregnated with an effective amount of potassium hydroxide applied to the carrier means whereby the apparatus is adapted to receive one or more vaginal fluid samples on the potassium hydroxide patch.

In accordance with a further aspect of the invention, there is provided a kit for the determining the presence or absence of vaginal infections comprising:

one or more carrier means, a patch impregnated with an effective amount of potassium hydroxide applied to one of the carrier means, and a first pH indicator means applied to one of the carrier means.

In accordance with a further aspect of the invention, there is provided a method for testing a vaginal fluid for the presence or absence of a vaginal infection, the steps that include:

providing a first pH indicator means and a potassium hydroxide patch on one or more carrier means, first applying the vaginal fluid to the first pH indicator means, subsequently applying the vaginal fluid to the potassium hydroxide patch, and then visually observing a colour change on the first pH indicator means and smelling the potassium hydroxide patch.

As mentioned above, diagnosis of BV may be made by the physician in his or her office when three or four criteria are met. This invention will allow the physician to easily perform the pH measurement (criteria 3) and KOH whiff test (criteria 4). The physician will also be able to observe the appearance of the vaginal fluid (criteria 2), thereby allowing for the diagnosis of BV according to the Amsel criteria. If BV is ruled out, there is also a need to easily determine the pH of the vaginal fluid to determine whether the patient has another vaginal infection since pH levels other than pH 4.5 are indicative of other conditions. For example, in the case of a yeast infection, the pH of the vaginal fluid will generally be pH 4.5 or lower.

BRIEF DESCRIPTION OF THE DRAWINGS

These and other aspects of the invention, as well as the details of an illustrative embodiment, will be more fully understood from the following drawings in which like numerals denote like parts in the several views, and in which:

FIG. 1 is a top plan view of a carrier stick apparatus in one embodiment of the invention; and FIG. 2 is a side view of the carrier stick apparatus of FIG. 1.

In the drawings, preferred embodiments of the invention are illustrated by way of example. It is to be expressly understood that the description and drawings are only for the purpose of illustration and as an aid to understanding preferred embodiments of the invention, and are not intended as a definition of the limits of the invention, as one skilled in the art would appreciate that other variations and modifications are possible within the scope of the invention as claimed.

DETAILED DESCRIPTION OF THE PREFERRED EMBODIMENT

Referring to the embodiment in FIG. (1), a carrier means in the form of an elongated, narrow carrier stick (1) has a first end (2) and a second end (3). A first pH indicator means (4) in the form of a pH strip is applied to the carrier means near the first end (2) of the carrier means and is buffered to provide a pH reading at a pH equal to 4.5. A second pH indicator means (5) in the form of a pH strip, spaced from and adjacent to the first pH indicator means (4) at the first end (2) of the carrier means, is buffered to provide a pH reading in a pH range of 3.0 and 6.0. The second pH indicator means (5) is used in the preferred embodiment to provide a confirmation of the pH reading from the first pH indicator means (4) and is preferably a different type of pH paper in order to confirm the reading obtained from the first pH indicator means (4). A potassium hydroxide ("KOH") patch (6) is applied to the second end of the carrier stick (3).

The first pH indicator means (4), the second pH indicator means (5) and the KOH patch (6) will not necessarily be attached to a single carrier means and may exist on separate carrier means or in any combination thereof. Also, either pH indicator means and the KOH patch may exist alone on a carrier means. It is also understood that a single pH indicator means can be used which indicates whether the pH is greater than or equal to 4.5 if the invention is being used to detect the presence of bacterial vaginosis.

While the embodiment shown in FIGS. 1 and 2 illustrates a carrier means in a form of a stick, the carrier means may, in alternate embodiments, be in the form of a disc or card or other means provided that the carrier means allows for the fixation of the pH indicator means and KOH patch on the carrier means to allow for ready application of a vaginal fluid sample to the pH indicator means and KOH patch. For example, the carrier means may consist of wood, plastic or other suitable material.

As shown in FIG. 1, the first pH indicator means (4) may comprise any suitable pH indicator strip which is available from various commercial manufacturers and is buffered to undergo a colour change at a pH equal to pH 4.5. The first pH indicator means (4) is adhered to the carrier means (1) by an adhesive which may be any commercially available adhesive suitable for adhering such materials and would include, for example, an acrylic, pressure-sensitive two sided adhesive tape such as those manufactured by 3M Company Canada Inc.

In the preferred embodiment, the second pH indicator means (5) indicates a sliding scale for pHs between 3.0 and 6.0. It is also a pH indicator strip available from numerous commercial manufacturers. The second pH indicator means (5) is also adhered to the carrier means (1) by an adhesive which may be any commercially available adhesive suitable for such materials such as an acrylic, pressure-sensitive two sided adhesive tape manufacturer as described above.

In the preferred embodiment, the pH of the vaginal fluid applied to the first pH indicator means (4) and the second pH indicator means (5) is determined by comparisons to a standard pH color comparison chart widely available from manufacturers of various pH strips. A pH color comparison chart provides a range of pHs and the colour for each pH. The pH colour comparison chart will enable the user of the apparatus to visually match the colour of the first pH indicator means (4) and the second pH indicator means (5) once the vaginal fluid is applied to the various pH indicator means) with their respective pH colour comparison charts thereby enabling the user to determine the approximate pH of the vaginal fluid. The pH color comparison charts may be provided in any manner, such as on packaging on one of the carrier means, or a separate enclosure to the carrier means, for example.

In the embodiment of FIGS. 1 and 2, the KOH patch (6) comprises a potassium hydroxide concentration of 10% to 20%. However, as known to one skilled in the art, the concentration of potassium hydroxide may be any effective amount that allows for the detection of bacterially-derived amines. The KOH patch (6) is applied to the carrier stick (1) via a similar type of adhesive as described above.

In one embodiment of the invention, the carrier means is a stick which 6 inches in length, ⅜ inch in width and 2 mm in thickness. The first pH indicator means (4) is a pH strip approximately ⅜"×¼" which is adhered to the carrier means (1) approximately ¼" from the first end (2) of the carrier means (1). The second pH indicator means (5) is a pH strip approximately ⅜×¼" which is adhered to the carrier means (1) approximately ½" from one end of the first pH indicator means (4).

In a second embodiment of the invention, the first pH indicator means and the KOH patch are attached to a carrier means, and the second pH indicator means is omitted. In a third embodiment of the invention, the second pH indicator means and the KOH patch are attached to a carrier means (and the first pH indicator is omitted). In a fourth embodiment, the KOH patch alone is attached to a carrier means.

It is preferred that the carrier means be stored at normal room temperature in an airtight container and not be exposed to light or extreme humidity. It is also recommended that the KOH patch be covered with a protective film to prevent accidental contact of a person's body parts with the KOH patch.

In operation, in the embodiment of the invention illustrated in FIGS. 1 and 2, the following steps are performed: a) vaginal fluid is obtained on a swab and applied to the first pH indicator means (4), the second pH indicator means (5) and the KOH patch (6), including fully coating both pH indicator means; (b) the first pH indicator means (4) and the second pH indicator means (5) are visually compared to commercially available pH color comparison charts in order to determine the approximate pH of the vaginal fluid; and c) the KOH patch is smelled. It is desirable that step a) be performed first to prevent the contamination of the pH indicator means by alkaline KOH. However, it is understood that steps b) and c) may be performed in reverse order. Preferably, steps b) and c) will take place within 20 to 40 seconds of the placement of the vaginal fluid sample on the pH indicator means and the KOH patch.

A pH of greater than or equal to 4.5 and a positive KOH whiff test will enable the physician to evaluate two of the four criteria required for the diagnosis of BV. The third criteria will be observation of the discharge as thin and homogeneous grey to white. The physician will therefore be able to diagnose BV quickly in his or her own office.

Furthermore, if BV is ruled out, the physician will also be able to determine the pH of the vaginal fluid to determine possible causes of vaginal infection such as yeast infections.

Person skilled in the art would recognize, or able to ascertain using no more than routine experimentation, many equivalents to the embodiments of the present invention. Such equivalents are contemplated and intended to be encompassed within the spirit and scope of the invention as defined in the following claims.

What is claimed is:

1. An apparatus for testing vaginal fluid for assessing the presence or absence of a vaginal infection, the apparatus comprising:

one or more carrier means, a patch impregnated with an effective amount of potassium hydroxide applied at least one carrier means, and a first pH indicator means applied to at least one carrier means, whereby the apparatus is adapted to receive one or more vaginal fluid samples on each of the potassium hydroxide patch and the first pH indicator means.

2. The apparatus of claim 1 wherein the first pH indicator means is capable of indicating a pH of 4.5 or greater.

3. The apparatus of claim 1 wherein the vaginal infection is selected from the group comprising bacterial vaginosis or yeast.

4. The apparatus of claim 1 wherein the vaginal fluid is tested for presence of bacterially-derived amines.

5. The apparatus of claim 1 wherein the potassium hydroxide patch comprises a potassium hydroxide concentration of 10% to 20%.

6. The apparatus of claim 1 further comprising a second pH indicator means capable of indicating a specific pH value within a pH range, the second pH indicator means applied to one of the carrier means.

7. The apparatus of claim 6 wherein the pH range is 3.0 to 6.0.

8. The apparatus of claim 1 wherein the carrier means is selected from the group comprising a stick, a disc or a card.

9. The apparatus of claim 1 wherein the carrier means is a stick, the stick having a first end and a second end, wherein the potassium hydroxide patch and the first pH indicator means are located at opposite ends of the stick.

10. The apparatus of claim 6 wherein the carrier means is a stick, the stick having a first end and a second end, wherein the potassium hydroxide patch is located near the first end of the stick and the first pH indicator means and the second pH indicator means are located near the second end of the stick.

11. The apparatus of claim 6 wherein the second pH indicator means is located near the first pH indicator means.

12. An apparatus for testing vaginal fluid for assessing the presence or absence of a vaginal infection, the apparatus comprising:

a carrier means, and a patch impregnated with an effective amount of potassium hydroxide applied to the carrier means whereby the apparatus is adapted to receive one or more vaginal fluid samples on the potassium hydroxide patch.

13. The apparatus of claim 12 wherein the vaginal infection is selected from the group comprising bacterial vaginosis or yeast.

14. The apparatus of claim 12 wherein the vaginal fluid is tested for the presence of bacterially-derived amines.

15. The apparatus of claim 12 wherein the potassium hydroxide patch comprises a potassium hydroxide concentration of 10% to 20%.

16. The apparatus of claim 12 wherein the carrier means is selected from the group comprising a stick, a disc or a card.

17. In a method for testing a vaginal fluid for the presence or absence of a vaginal infection, the steps that include:

providing a first pH indicator means and a potassium hydroxide patch on one or more carrier means, first applying the vaginal fluid to the first pH indicator means, subsequently applying the vaginal fluid to the potassium hydroxide patch, and then visually observing a colour change on the first pH indicator means and smelling the potassium hydroxide patch.

18. The method of claim 17 further comprising:

providing a second pH indicator means on a carrier means, applying the vaginal fluid to the second pH indicator means, subsequently visually observing a colour on the second pH indicator means, and subsequently visually matching the colour on the second pH indicator means with a pH colour comparison chart.

19. The method of claim 17 wherein the potassium hydroxide patch is smelled for the presence of bacterially-derived amines.

20. The method of claim 17 wherein the vaginal infection is selected from the group comprising bacterial vaginosis or yeast.

21. The method of claim 17 wherein the potassium hydroxide patch is smelled within 20 to 40 seconds of application of the vaginal fluid to the potassium hydroxide patch.

* * * * *